United States Patent [19]

Ennis, III

[11] Patent Number: 4,923,448

[45] Date of Patent: May 8, 1990

[54] SYRINGE WITH SPRAY NOZZLE TIP

[75] Inventor: James F. Ennis, III, Preston, Conn.

[73] Assignee: Mark Anderson, Elmwood, Wis.

[21] Appl. No.: 280,331

[22] Filed: Dec. 6, 1988

[51] Int. Cl.⁵ .......................................... A61M 5/325
[52] U.S. Cl. .................................................. 604/239
[58] Field of Search ............. 604/239, 275, 279, 243, 604/242, 241, 240, 164, 165, 310, 311

[56] References Cited

U.S. PATENT DOCUMENTS 4,767,416 8/1988 Wolf et al. ........................ 604/239

Primary Examiner—John D. Yasko

Attorney, Agent, or Firm—Edward H. Loveman

[57] ABSTRACT

A syringe for dispensing a liquid as an atomized spray has a cylindrical barrel, a plunger movable axially in the barrel, a tubular nozzle at one end of the barrel, and a short fixed stem in the nozzle. A cup shaped nozzle tip has internal first spaced lands to frictionally engage the stem and define axially extending passages therebetween. A centrally apertured end wall of the nozzle tip has circumferentially spaced second lands to serve as abutments for the end of the stem. Troughs in the end wall between the second lands define further passages with the end of the stem for turbulently passing the liquid out of the aperture as an atomized spray.

10 Claims, 3 Drawing Sheets

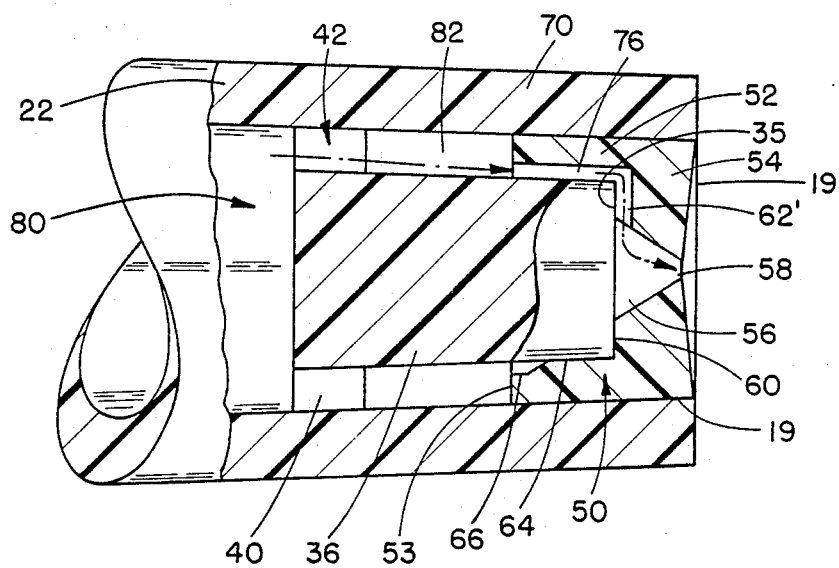
FIG.5
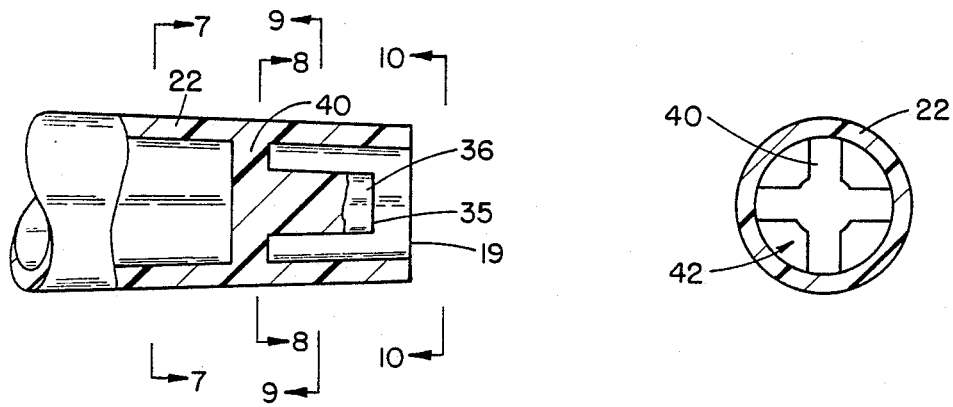
FIG.6
FIG.7
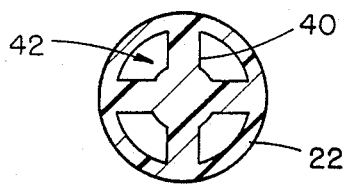
FIG.8
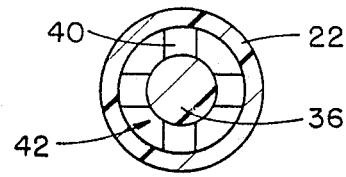
FIG.9

20

SYRINGE WITH SPRAY NOZZLE TIP

BACKGROUND OF THE INVENTION

1. Field of the Invention

This invention relates to the art of syringes for dispensing liquids such as medicaments, and more particularly concerns a syringe with a long nozzle provided with a novel tip which discharges the liquid contents of the syringe as an atomized liquid spray.

2. Description of the Prior Art

Conventional syringes of the hypodermic type generally employ needles removably mounted at the nozzle end for injecting medicaments subcutaneously. Such a hypodermic syringe emits a fine stream under pressure but it cannot be used to administer a medicinal liquid spray which is often required for an ear, eye, nose, throat or other body part. If the needle is removed from the nozzle of the syringe there is left a rather wide opening which is too large to administer a proper spray.

SUMMARY OF THE INVENTION

According to the invention there is provided a novel nozzle tip which adapts a conventional syringe to emit an atomized spray when liquid is forced out under pressure by a plunger in the syringe. The invention is adapted for use with a syringe having a plunger advanced by finger pressure applied directly or via a trigger mechanism, such as in syringes of the automatic type. The new nozzle tip is a miniature cup shaped body having flat, spaced lands which abut sides and ends of a short, fixed axial stem in the nozzle of the syringe. Axially extending first passages are defined by the lands along the stem. Inside the nozzle tip at its apertured end is a plurality of troughs between the lands, to define second passages for liquid forced turbulently out of the nozzle tip. The second passages terminate in an axial funnel leading to a small central aperture from which the turbulent liquid is discharged as an atomized spray. Thus, the new nozzle tip adapts a conventional syringe to dispense a medication as an atomized spray, internasally, interocularly, orally, otically, tracheally, etc.

These and other objects and many of the attendant advantages of the invention will be readily appreciated as the same becomes better understood by reference to the following detailed description when considered in connection with the accompanying drawings in which:

BRIEF DESCRIPTION OF THE DRAWINGS

FIG. 5 is an enlarged fragmentary longitudinal sectional view of the syringe nozzle and nozzle tip, taken along line 5—5 of FIG. 1, ;

FIG. 6 is a longitudinal sectional view on an enlarged scale of part of the syringe nozzle per se, on a large scale, with the nozzle tip removed;

FIGS. 7, 8 and 9 are cross sectional views taken along respective lines 7—7, 8—8, and 9—9 of FIG. 1;

DESCRIPTION OF THE PREFERRED EMBODIMENT

Figure 1:
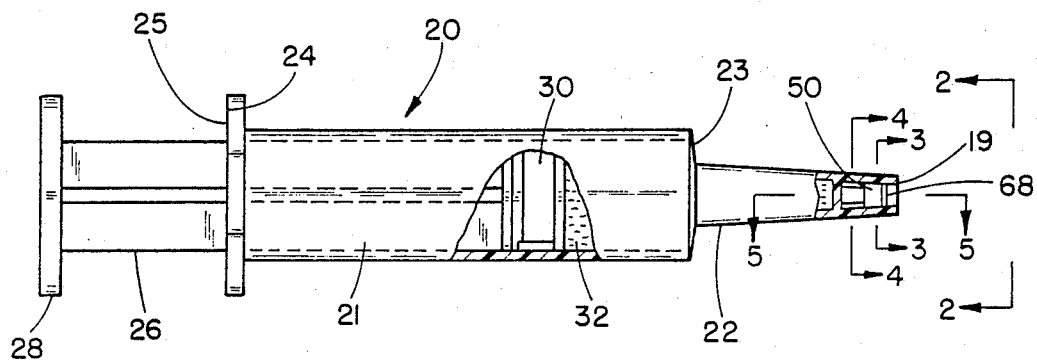
FIG. 1 is a side elevational view of a syringe embodying the invention.
Figure 2:
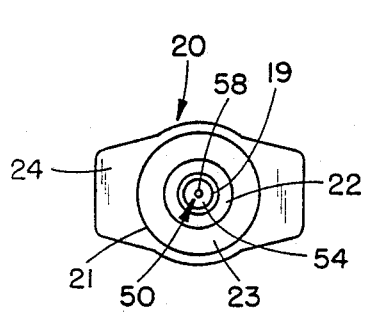
FIG. 2 is an end elevational view of the syringe taken along line 2—2 of FIG. 1.

Referring now to the drawings wherein like reference characters designate like or corresponding parts throughout, there is illustrated in FIGS. 1 and 2 a syringe, generally designated as reference numeral 20, which has a long cylindrical barrel 21 terminating at one end 23 in an elongated tapering tubular nozzle 22, having an open end 19. At the other open end 25 of the barrel 21 is an external integral flange 24 which serves as a finger grip. Axially movable in the barrel 21 is a long plunger 26, at the outer end of which is a head 28, which facilitates advancing the plunger 26 in the barrel 21. At the inner end of the plunger 26 is a rigid piston head 30 which forces a liquid 32 out of the barrel 21 and through the tubular nozzle 22 when the plunger 26 is advanced to the right as viewed in FIG. 1. In the nozzle 22, spaced a short distance from the nozzle open end 19, as best illustrated in FIGS. 6-10, is a short fixed, axial, cylindrical stem 36, which may be integral and extends forwardly from the center of four radial spider arms 40, each of which is spaced 90 apart to rigidly support the stem 36. The four angular spaced arms 40 and the stem 36, define four axially extending circumferentially spaced passages 42 for liquid 32 discharging through the nozzle. The stem 36, terminates a short distance from the nozzle open end 19, with a flat free end 35.

According to the invention there is further provided a novel nozzle tip 50 as illustrated in FIGS. 3-5 and 11-15 which has a cup shaped body with a cylindrical wall 52, open at a rear annular end 53. At the other end, the cup shaped nozzle tip 50, is closed by a circular wall 54, which is slightly bowed or concave inwardly and formed with a conical or funnel shaped passage 56 terminating in a narrow central opening or aperture 58. The inner side of the end wall 54 is formed with three generally triangular flat lands 60 spaced angularly apart around the wider end of the conical passage 56. The three lands alternate with three generally triangular troughs 62. At the inner side of the cylindrical wall 52 are three flat lands 64, each respectively aligned with a different one of the lands 60, and spaced angularly apart and terminating at the lands 60. The lands 64 have tapered ends 66 extending toward the open end 53 of the nozzle tip 50. At the outer side of the wall 52 is a circumferential bead 68. The wall 52 is flexible so that the bead 68 insures that the tip 50 forms a firm frictional grip with the inside of a tubular wall 70 of the nozzle 22.

Figure 3:
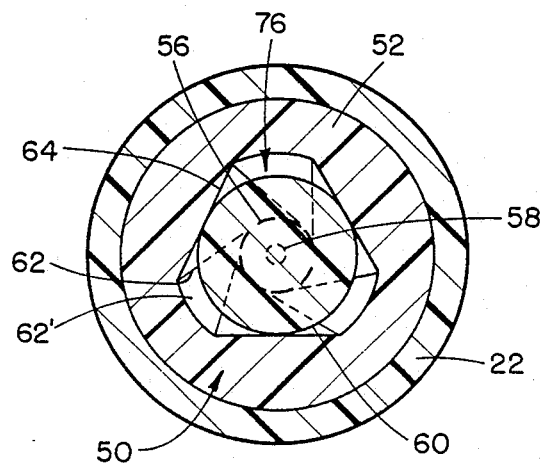
FIGS. 3 and 4 are enlarged cross sectional views of the tubular nozzle of the syringe taken along respective lines 3—3 and 4—4 of FIG. 1.
Figure 4:
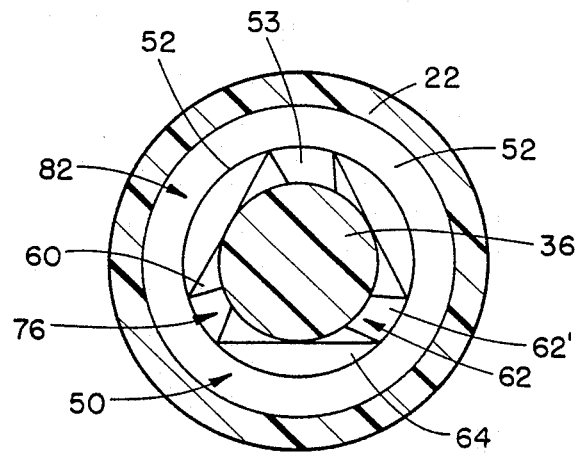
Figure 10:
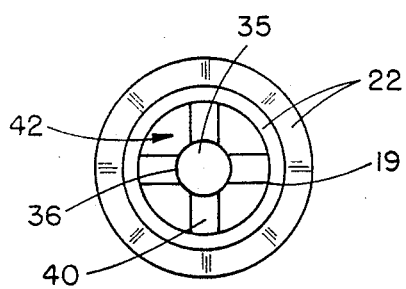
FIG. 10 is an end elevational view taken along line 10—10 of FIG. 6.
Figure 11:
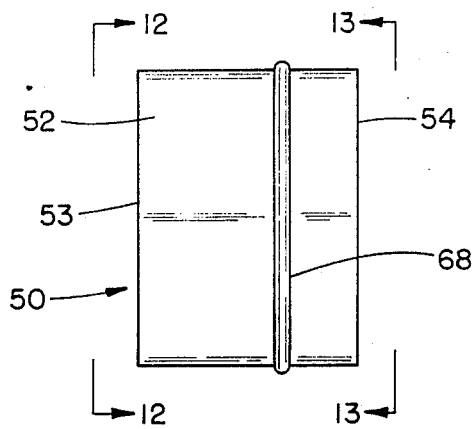
FIG. 11 is a side elevational view on an enlarged scale of the nozzle tip per se.
Figure 12:
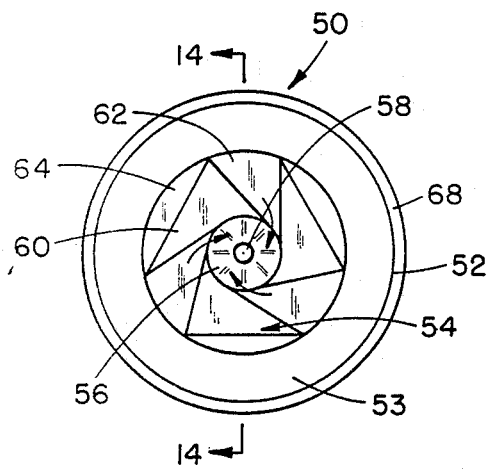
FIGS. 12 and 13 are opposite end elevational views taken along respective lines 12—12, and 13—13 of FIG. 11.
Figure 13:
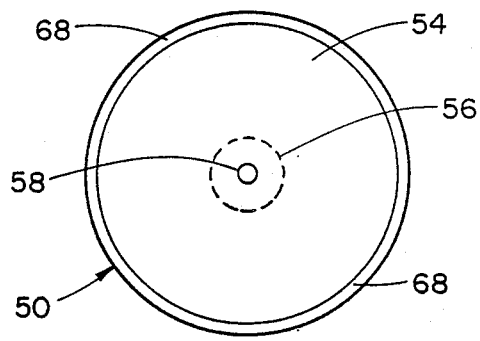
Figure 14:
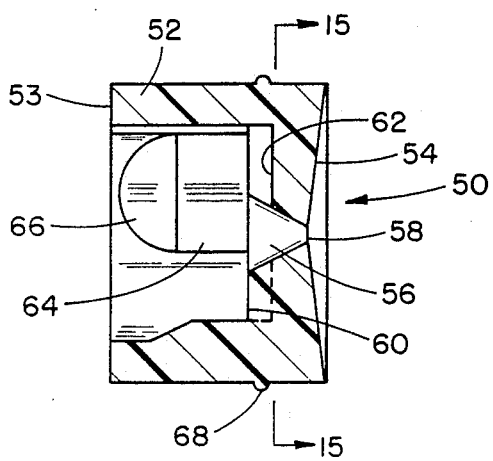
FIG. 14 is a longitudinal sectional view taken along line 14—14 of FIG. 12.
Figure 15:
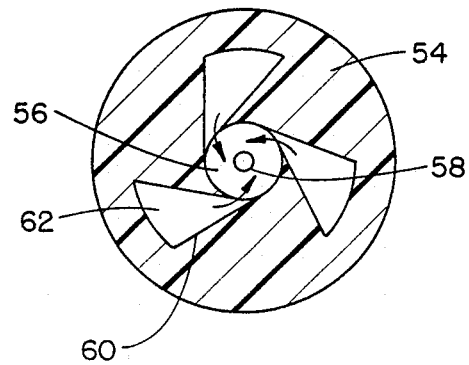
FIG. 15 is a cross-sectional view taken along line 16—16 of FIG. 14.

When the nozzle tip 50 is installed in the nozzle 22, the stem 36 fits snugly, laterally, within the lands 64, which grip the stem 36, tangentially; see FIGS. 3, 4, and 5. The stem 36 extends axially along the full length of the interior of the nozzle tip 50, until a flat circular end 35, of the stem 36, abuts and seats against the land 60. Three angularly spaced passages 62', are then defined between the end 35 of the stem 36, the troughs 62.

Three axially extending passages 76 are defined between the lands 64, the inner side of the wall 52, and the stem 36, as best shown in FIGS. 3 and 5. By the arrangement described, when the nozzle tip 50 is fully seated in place in the nozzle 22, as clearly shown in FIG. 5, direct communication is provided (as indicated by arrows) from a nozzle bore 80, through the four passages 42, through a tubular passage 82, defined between the stem 36, and the inner side of the nozzle 22, through the three lateral passages 76, through the three triangular, circumferentially spaced passages 62'; and through the conical passage 56 to the central aperture 58. The liquid is emitted as a turbulent atomized spray from the aperture 58. The greater the axially pressure applied to the plunger 26, the greater will be the velocity and turbulence of the liquid spray issuing from the nozzle tip 50. It is possible to increase the atomization of the spray somewhat, by withdrawing the plunger 26 slightly in the barrel 21, to admit air into the nozzle 22. Then when the plunger is forced forwardly, the air will mix turbulently with the liquid in the tortuous passages, to exit as a highly dispersed atomized stream of liquid.

The nozzle tip 50 may be used with any suitable syringe, such as one which normally uses removable needles for subcutaneous injections. The insertion of the stem 36 and the nozzle tip 50 will convert the syringe to a highly efficient and effective sprayer of liquid medicament or other liquid The nozzle tip 50 can easily be removed from the nozzle 22, by insertion of a stiff wire or narrow rod through the barrel 21 from the open end 25, through the passage 42 and through the passage 82, to contact the inner annular end 53 of the wall 52 of the nozzle tip 50, and to push the nozzle tip 50 out of the nozzle 22.

In one practical embodiment, the cylindrical wall 52 of the nozzle tip 50 has an external diameter of about 0.180 inches and an axial length of about 0.150, and a maximum wall thickness, at lands 64 of about 0.020 inches. The thickness of the bead 68 was about 0.002 inches. The stem 36 of the nozzle 22 had an axial length of about 0.185 inches and terminated about 0.060 inches from the open end 19 of the nozzle 22. The inside diameter of the nozzle 22, at the opening 19, was about 0.0185 inches. The spider arms 40 were spaced about 0.250 inches from the open end 19 of the nozzle 22. When the nozzle tip 50 was seated in place with the free outer end 35 of the stem 36 in abutment with the lands 56, the cylindrical wall 52 of the nozzle tip 50 extended only part of the distance from the nozzle opening 19 to the arms 40, to define the tubular passage 82, between the arms 40 and the inner end 53 of the nozzle tip 50. The aperture 58 in the end wall 54 of the nozzle tip 50 was about 0.005 inches to produce a fine atomized, turbulent spray of liquid from the syringe.

The nozzle tip 50 and the stem 36 may be manufactured from any suitable flexibile plastic material, such as polyethylene, polyvinyl, etc., at very low cost, by mass production molding processes; so that the nozzle trip 50 may be discarded after one or several uses.

It should be understood that the foregoing relates to only a preferred embodiment of the invention, which has been by way of example only, and that it is intended to cover all changes and modifications of the example herein chosen for the purpose of the disclosure, which do not constitute departures from the spirit and scope of the invention.

What is claimed is:

1. A syringe for dispensing a liquid atomized spray, comprising:

a cylindrical barrel having a chamber for containing a liquid and an open end;
   an axially movable plunger in said chamber for discharging said liquid through said open end of said barrel;
   a nozzle having a tubular wall secured to said open end of said barrel and having a free open end for discharging said liquid therefrom;
   a stem axially disposed in fixed position in said nozzle and radially spaced from said tubular wall to define therewith a tubular first passage, said stem having a free end spaced inwardly from said open end of said nozzle; and
   a cup shaped nozzle tip axially disposed in said nozzle, said nozzle tip comprising:
      a cylindrical wall engaged on said stem to provide axially extending second passages therebetween communicating with said tubular first passage,
      an end wall integral with said cylindrical wall and formed with an aperture for discharging said liquid therefrom as an atomized spray; and
      troughs on said end wall defining with said free end of said stem third passages communicating with said second passages and said aperture to pass said liquid turbulently to and through said aperture to and thereby produce said atomized spray.

2. A syringe as defined in claim 1, further comprising circularly spaced radially extending spider arms in said nozzle for axially supporting said stem, said arms defining therebetween further passages communicating with said tubular first passage to pass said liquid from said chamber barrel, through said tubular first passage, and through said further passages, when said plunger is advanced in said barrel.

3. A syringe as defined in claim 1, wherein said cylindrical wall of said nozzle tip is formed with a plurality of lateral circumferentially spaced lands frictionally engaging said stems, said second passages being spaced apart circumferentially of said cylindric wall between said lands to divide said liquid into separate streams.

4. A syringe as defined in claim 3, further comprising circumferentially spaced other lands on said end wall of said nozzle tip at said first named lands to serve as abutments at said free end of said stem.

5. A syringe as defined in claim 4, wherein said troughs are disposed between said other lands and circumferentially spaced apart on said end wall to define third passages with said free end of said stem.

6. A syringe as defined in claim 5, further comprising circumferentially spaced and radially extending spider arms fixed in said nozzle and axially supporting said stem, said arms defining therebetween further passages communicating with said tubular first passage to pass said liquid from said chamber barrel through said tubular first passage and said further passages when said plunger is advanced in said barrel.

7. In an improved syringe for producing an atomized liquid spray, said syringe of the type having a cylindrical barrel for containing a liquid, with a plunger movable axially in said barrel to discharge said liquid therefrom, and a tubular nozzle at one end of said barrel with an open free end for discharging said liquid, said improvement comprising:

a fixed axial stem in said nozzle near said open end of said nozzle;
   a cup shaped body axially disposed in said open end of said nozzle and having a cylindrical wall engageable on said stem and adapted to provide axially extending passages therebetween to pass said liquid from said nozzle through said body, said body having an end wall formed with an aperture for discharging said liquid from said body as an atomized spray, and troughs, formed in said end wall, for defining with an end of said stem, other passages, communicating with said axially extending passages and said aperture, to produce said atomized liquid spray.

8. An improved syringe as defined in claim 7, wherein said cylindrical wall is formed with a plurality of lateral circumferentially spaced lands for frictionally engaging said stem, said axially extending passages being spaced apart circumferentially of said body between said lands to divide said liquid into separate streams.

9. An improved syringe as defined in claim 8 further comprising circumferentially spaced other lands on said end wall at said first named lands, to serve as abutments at said free end of said stem.

10. An improved syringe as defined in claim 9, wherein said troughs are disposed between said other lands to define said other passages.

* * * * *